(12) United States Patent
Fei et al.

(10) Patent No.: US 8,073,230 B2
(45) Date of Patent: Dec. 6, 2011

(54) SYSTEMS AND METHODS FOR GENERATING IMAGES FOR IDENTIFYING DISEASES

(75) Inventors: Baowei Fei, Lyndhurst, OH (US); Robert Gilkeson, Cleveland Hts., OH (US)

(73) Assignee: Case Western Reserve University, Cleveland, OH (US)

( * ) Notice: Subject to any disclaimer, the term of this patent is extended or adjusted under 35 U.S.C. 154(b) by 808 days.

(21) Appl. No.: 12/118,232

(22) Filed: May 9, 2008

(65) Prior Publication Data

US 2009/0279761 A1 Nov. 12, 2009

(51) Int. Cl.
G06K 9/00 (2006.01)
(52) U.S. Cl. ........................................................ 382/132
(58) Field of Classification Search ........... 382/128–132
See application file for complete search history.

(56) References Cited

U.S. PATENT DOCUMENTS

| | | | |
|---|---|---|---|
| 2007/0047794 A1* | 3/2007 | Lang et al. | 382/132 |
| 2007/0196007 A1* | 8/2007 | Chen et al. | 382/131 |
| 2007/0206880 A1* | 9/2007 | Chen et al. | 382/294 |
| 2009/0226058 A1* | 9/2009 | Li et al. | 382/128 |
| 2009/0279761 A1* | 11/2009 | Fei et al. | 382/130 |
| 2009/0285361 A1* | 11/2009 | Akahori | 378/98.11 |

OTHER PUBLICATIONS

Chen et al: "Automatic 3D-to-2D Registration for CT and Dual-Energy Digital Radiography for Calcification Detection"; Med. Phys.34 (12), Dec. 2007, Am. Assoc. Phys. Med., pp. 4934-4943.
Fei et al: "Automatic Registration of CT Volumes and Dual-Energy Digital Radiography for Detection of Cardiac and Lung Diseases"; Proceedings of the 28th IEEE EMBS Annual International Conference New York City, USA, Aug. 30-Sep. 3, 2006, pp. 1976-1979.
Coselmon et al: "Mutual Information Based CT Registration of the Lung at Exhale and Inhale Breathing States Using Thin-Plate Splines"; Med. Phys. 31 (11), Nov. 2004, AM. Assoc. Phys. Med. 2004, pp. 2942-2948.

* cited by examiner

Primary Examiner — Jingge Wu
(74) Attorney, Agent, or Firm — Tarolli, Sundheim, Covell & Tummino LLP

(57) ABSTRACT

Systems and methods for generating images for identifying diseases are provided. In one embodiment, a method comprises receiving a first digital radiography (DR) image of at least a portion of a body of a patient, receiving a second DR image of the at least a portion of a body of a patient, the first DR image being captured at a different energy level than the second DR image, and determining common control point locations for both the first and second DR images. The method further comprises generating an optimized DR image by moving portions of a selected one of the first and second DR images with its associated control points to locations that correspond to similar portions of the other of the first and second DR images, applying deformable transformation to one of the first and second DR images and performing a log subtraction on the first and second DR image to generate a dual-energy digital radiography (DEDR) image.

16 Claims, 5 Drawing Sheets

Dual-energy Image

Reconstructed Image from CT

CT Image

3D Rendering from CT

SYSTEMS AND METHODS FOR GENERATING IMAGES FOR IDENTIFYING DISEASES

RELATED APPLICATIONS

The present invention claims priority from U.S. Provisional Patent Application No. 60/916,584, filed 8 May 2007, the entire contents of which is incorporated herein.

FIELD OF THE INVENTION

The present invention relates to imaging, and particularly relates to systems and methods for generating images for identifying diseases.

BACKGROUND

Cardiovascular disease is a leading cause of death in the United States, and responsible for approximately 500,000 deaths per year. More than one million Americans have heart attacks or angina every year. The increasing incidence of cardiovascular disease makes accurate and noninvasive imaging of early cardiovascular disease increasingly important. Recently, digital radiography (DR) has markedly improved imaging of cardiac and lung diseases. Digital technology has enabled the use of dual-energy techniques in digital radiography systems. With recent advancements in digital radiography and flat-panel technology, dual-energy subtraction techniques can produce a high-energy image and a low-energy image. Post-processing of these two images results in the following images: a standard high-energy image, a subtracted soft-tissues image that removes overlying bone from the underlying lung and mediastinum, and a low-energy bone image that optionally displays bone and calcified thoracic structure. Thus, dual-energy digital radiography could be a cost-effective screening tool for cardiac and lung diseases.

However, cardiac and/or lung motion causes artifacts on the subtracted images, resulting in inconsistent detection and diagnosis of cardiac and lung diseases. Though the high-energy and low-energy images are taken within a very short period of time, they still represent different phases of the cardiac and respiration motion cycles. Because the two images may not be perfectly aligned, subtracting one image from the other will generate motion artifacts and reduce the image quality.

SUMMARY OF THE INVENTION

The present invention relates to systems and methods for generating images for identifying diseases. In one aspect of the invention, a method comprises receiving a first digital radiography (DR) image of at least a portion of a body of a patient, receiving a second DR image of the at least a portion of a body of a patient, the first DR image being captured at a different energy level than the second DR image, and determining common control point locations for both the first and second DR images. The method further comprises generating an optimized DR image by moving portions of a selected one of the first and second DR images with its associated control points to locations that correspond to similar portions of the other of the first and second DR images, applying deformable transformation to one of the first and second DR images and performing a log subtraction on the first and second DR image to generate a dual-energy digital radiography (DEDR) image.

In another aspect of the invention, a system for generating images for identifying diseases is provided. The system comprises a control point optimization component configured to receive a first digital radiography (DR) X-ray image captured at a first energy level and a second DR X-ray image captured at a second energy level of at least a portion of a body of a patient and configured to optimize a DR X-ray image by moving portions of a selected one of the first and second DR X-ray images to locations that correspond to similar portions of the other of the first and second DR X-ray images. The system further comprises a deformable transformation component that applies a deformable transformation to one of the first and second DR X-ray images and a log subtraction component that performs a log subtraction on the first and second DR X-ray image to generate a DEDR image.

In another aspect of the invention, a method for generating images for identifying diseases is provided. The method comprises receiving a three-dimensional computer tomography (CT) image, performing a 3-dimensional (3D) translation and rotation on the CT image and projecting the CT image onto an image plane to generate a 2-dimensional (2D) digitally reconstructed radiography (DRR) image. The method further comprises performing a 2D transformation on the 2D DRR image, measuring similarities of the 2D DRR with a dual-energy digital radiography (DEDR) image and optimizing the registration of the 2D DRR with the DEDR image.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The present invention relates to systems and methods of generating images that can be employed for identifying diseases, such as cardiac calcification and other cardiac and lung diseases. In one aspect of the invention, the generated images are dual-energy digital radiography (DEDR) X-ray images, such as a bone image and a soft tissue image generated from a high energy digital radiography (DR) image and a low energy DR image. In another aspect of the invention, a methodology is provided for transforming a three-dimensional computed tomography (CT) image into a two-dimensional digitally reconstructed radiography (DRR) image and aligning the DRR image with a DEDR X-ray image. The DRR image can be employed to confirm the identification of diseases in the DEDR image. The present invention provides for significant improvements in the generating of patient images that can be employed to locate diseases, such as cardiac calcification.

Figure 1:
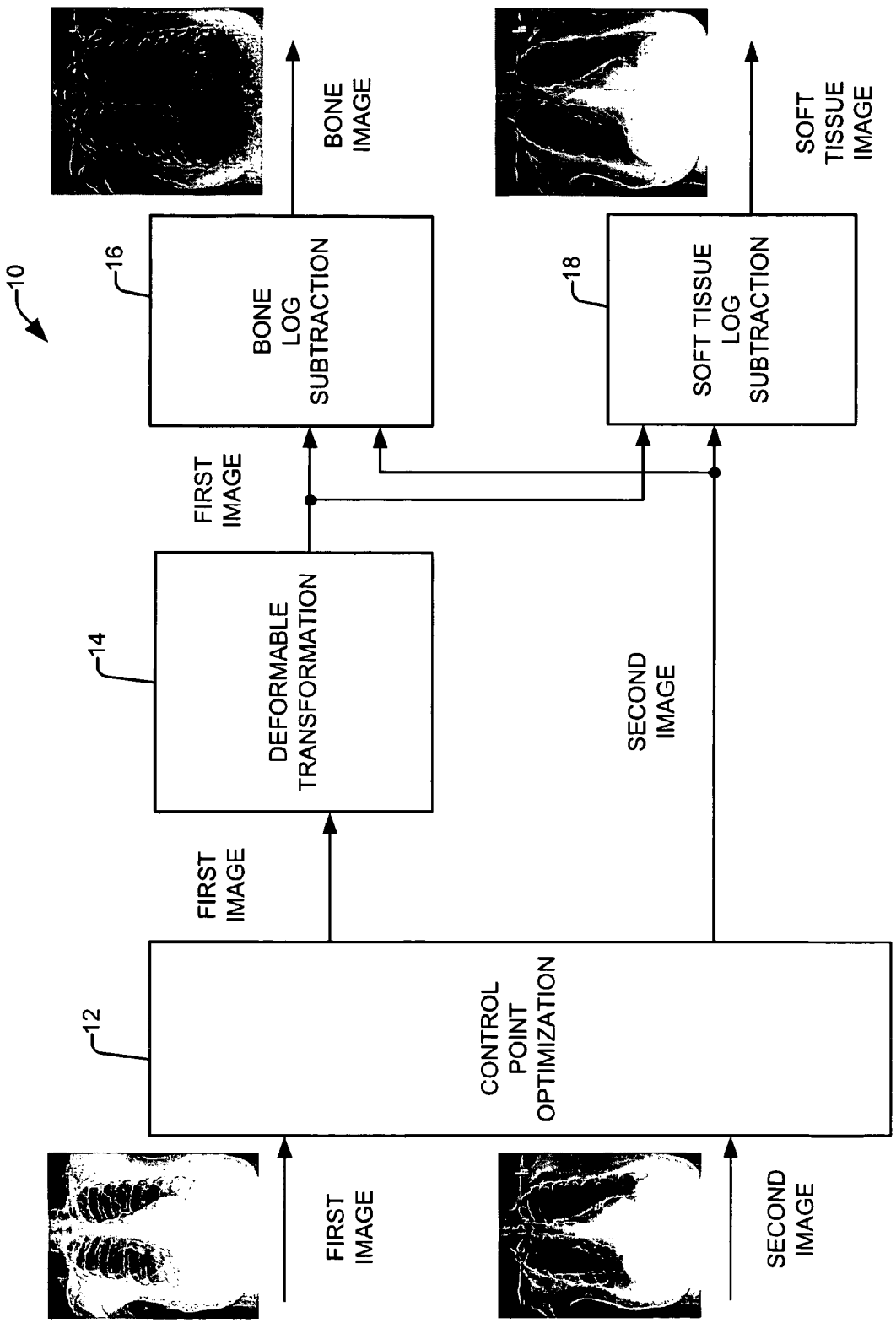
FIG. 1 illustrates a system for generating images for identifying diseases in accordance with an aspect of the present invention.

FIG. 1 illustrates a system 10 for generating images for identifying diseases in accordance with an aspect of the present invention. Although FIG. 1 is illustrated as a system 10, it is to be appreciated that the system 10 can be readily implemented as a methodology that employs computer executable components. It is further appreciated that the system can be one or more computer systems that execute the components of the system 10. The system 10 includes a control point optimization component 12 that receives a first DR X-ray image of at least a portion of a body (e.g., heart, lung) of a patient and a second DR X-ray image of the at least a portion of a body of a patient. The control point optimization component 12 can be a software algorithm and/or hardware device. The first DR X-ray image is captured at a first energy level and the second DR X-ray image is captured at a second energy level. For example, one energy level can be about 100 kVp to about 180 kVp and the other energy level can be about 40 kVp to about 100 kVp. The first DR X-ray is captured at a first time and the second DR X-ray is captured at a second time shortly after the first time (e.g., about 50 to about 500 ms), so that movement of the at least a portion of the body of the patient is mitigated. The first and second DR X-ray images are composed of a plurality of pixel intensity values and pixel coordinates that can be preprocessed to filter out noise and remove errors. The control point optimization component 12 is employed to remove misregistration of the second DR X-ray image relative to the first DR X-ray image caused by lung and/or heart motion of the patient.

The control point optimization component 12 determines common control point locations for both the first DR X-ray image and the second DR X-ray image. For example, the control point optimization component 12 can divide the first and second DR X-ray images into a plurality of grids, such that each grid of the first DR X-ray image has an associated grid in the second DR X-ray image, and determine a common center point for each of the plurality of grids for both the first and second DR X-ray image. The common center points can be employed as control points for the plurality of grids. Alternatively, edge features of the first and second DR X-ray image can be employed at control points, such that each edge feature is associated with a respective portion of the image.

The control point optimization component 12 performs an optimization routine on each control point and associated grid or image portion of a selected image (e.g., first image) relative to a non-selected image (e.g., the second image) by determining a similarity of image pixel intensity values of the associated grid or image portion and moving that associated grid or image portion of the selected to a location where similarities are determined on the non-selected image. This is repeated for each control point and associated grid or image portion until the selected image is registered with the non-selected image. The similarity can be determined by a simple subtraction routine of image pixel intensity values, such the lowest subtraction values represent the best matched between pixels. Alternatively, a mutual information statistical analysis or correlation coefficient computation can be performed to determine the best matched pixels. One image pixel intensity value of overlapping pixel intensity values of grids or image portions can be selected or the overlapping pixel intensity values can be averaged. Image pixel intensity values that move outside the image can be removed.

Once the selected image is aligned with the non-selected image, a deformable transformation algorithm 14 can be applied to one of the images. In the example of FIG. 1, the deformable transformation algorithm 14 is applied to the first image, however, the deformable transformation algorithm 14 can alternatively be applied to the second image. The deformable transformation algorithm 14 further facilitates the registration process by removing misregistration and deformation caused by lung and/or heart motion. The deformable transformation algorithm 14 can be, for example, a thin-plate spline (TPS) or B-Spline modeled algorithm.

Both the first image and the second image are then provided to a bone log subtraction algorithm 16 and a soft tissue log subtraction algorithm 18. The bone log subtraction algorithm 16 can be determined by the following equations:

$$I_L = I_{o,L} \cdot e^{-(\mu_{B,L} \cdot x_B + u_{S,L} \cdot x_S)}$$

$$I_H = I_{o,H} \cdot e^{-(\mu_{B,H} \cdot x_B + u_{S,H} \cdot x_S)} \qquad \text{EQ. 1}$$

$$I_{bone}(x, y) = \frac{I_H(x, y)}{I_L(x, y)^w} \qquad \text{EQ. 2}$$

Solving for $X_B$ and $X_S$ provides the bone image;

$$w = \frac{\mu_{S,H}}{\mu_{S,L}}$$

where $$\mathrm{Log} I_{bone}(x,y) = \mathrm{Log} I_H(x,y) - w \mathrm{Log} I_L(x,y) \qquad \text{EQ. 3}$$

where $I_H$ is the image intensity values of the high-energy image, $I_L$ is the image intensity values of the low-energy image, X and Y are the pixel coordinate values with w being the equation coefficient. The soft tissue log subtraction algorithm 18 can be determined by the same equations as the bone log subtraction equations except with a different w coefficient since soft tissue attenuates X-ray differently at different energies than bone. The bone and soft tissue image are both DEDR images that can be employed to locate diseases, such as cardiac calcifications.

Figure 2:
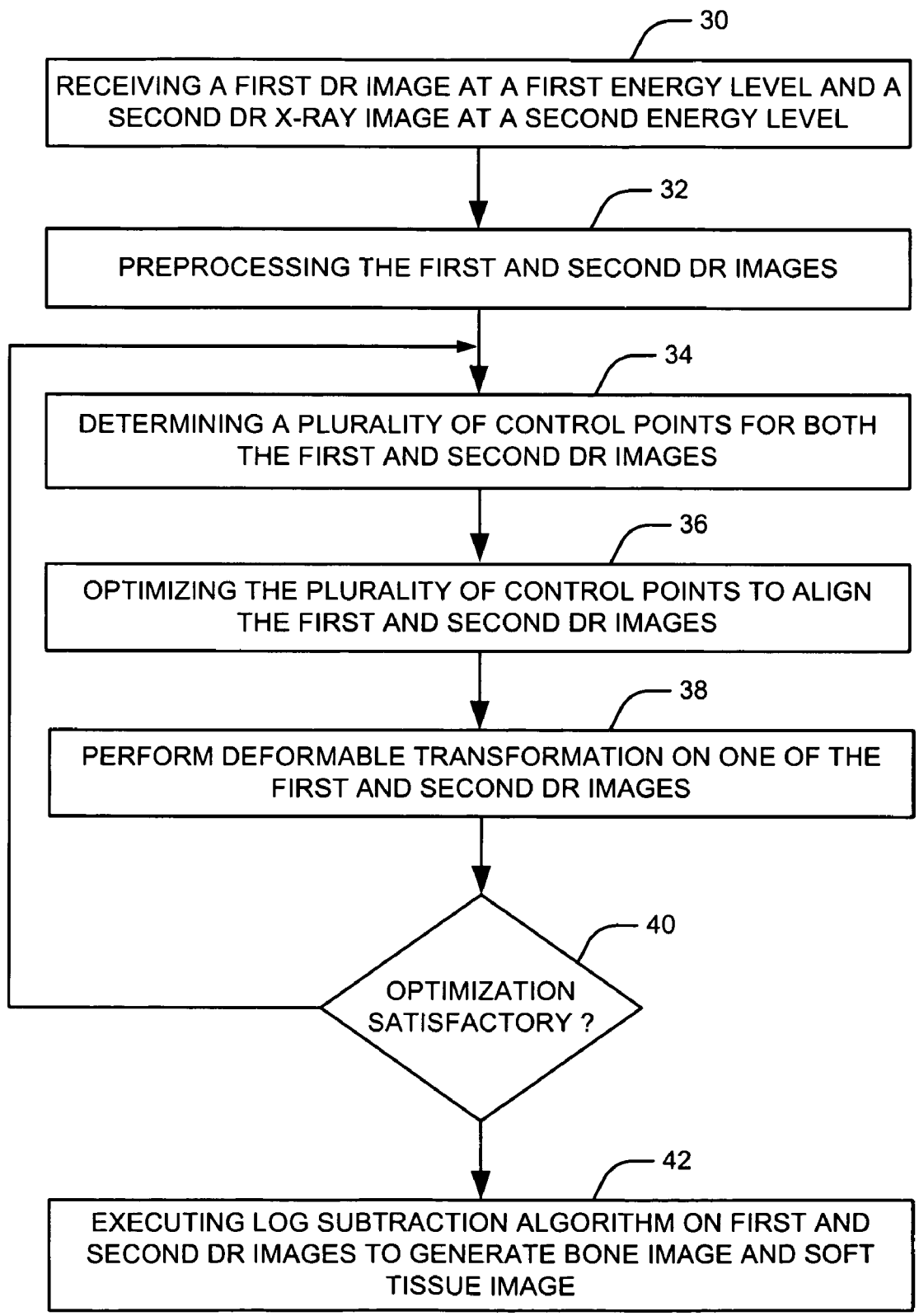
FIG. 2 illustrates a method for generating images for identifying diseases in accordance with an aspect of the present invention.

FIG. 2 illustrates a method for generating images for identifying diseases in accordance with an aspect of the present invention. The methodology begins at 30 where a first DR image captured at a first energy level and a second DR image captured at a second energy level are received. The first and second DR images are images of at least a portion of a body of a patient captured subsequently in time within a short time period to mitigate lung and/or heart motion of the patient. At 32, the first and second DR images are preprocessed to filter out noise and remove errors. At 34, a plurality of control points are determined for both the first and second DR images. The control points can be located at a central point of a plurality of grids of both the first and second DR images, or at edges of grids and/or the first and second DR images. At 36, the plurality of control points are optimized to align the first and second DR images to mitigate misalignment due to lung and/or heart motion of the patient during the subsequent capturing of the first and second DR images. At 38, deformable transformation is performed on one of the first and second DR images. At 40, it is determined if the optimization is satisfactory. If the optimization is not satisfactory (NO), the methodology returns to 34 to repeat the determining and optimization of the control points. If the optimization is satisfactory (YES), the methodology proceeds to 42. At 42, log subtraction algorithms are executed to generate a bone image and a soft tissue image from the optimized and transformed first and second DR images.

Figure 3:
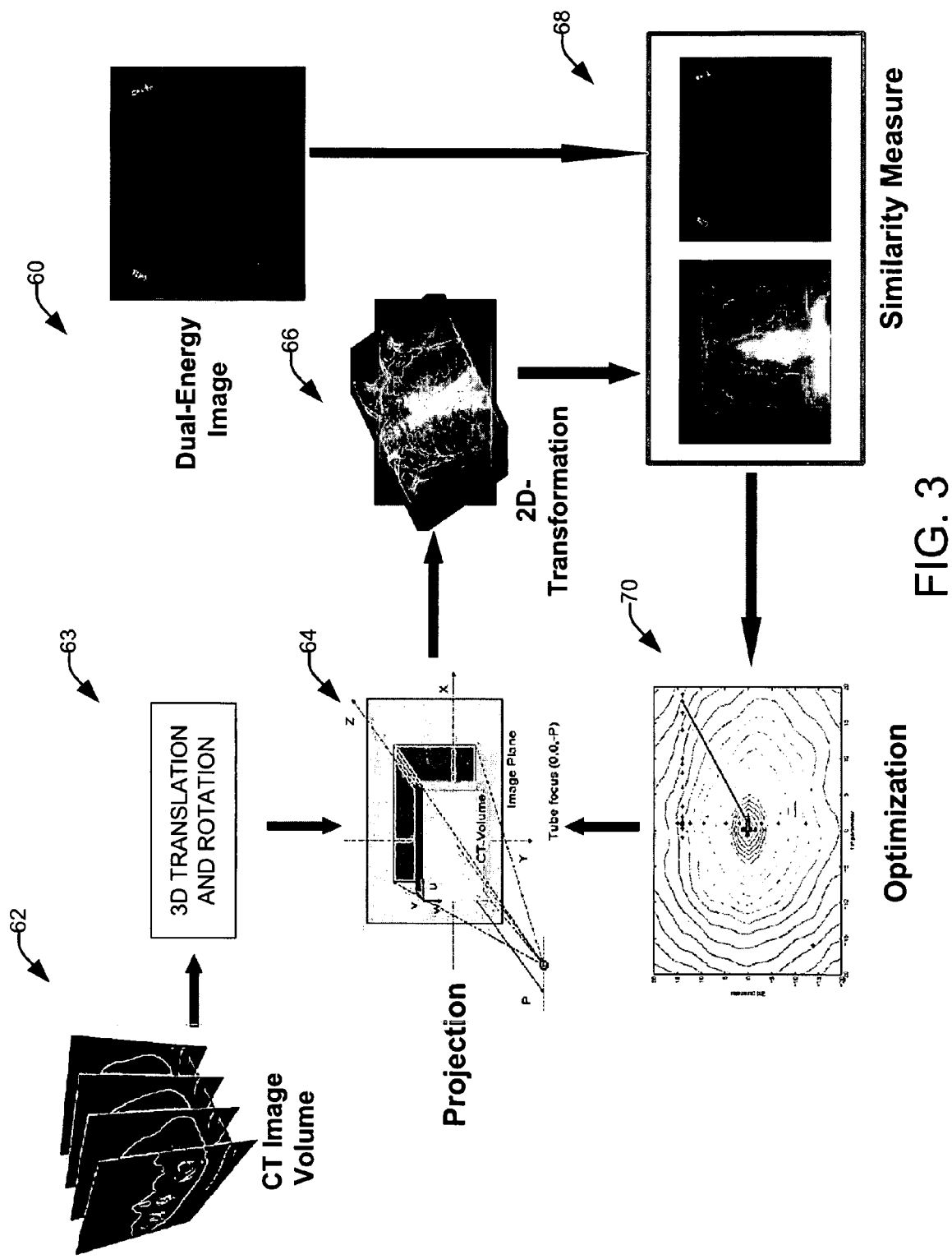
FIG. 3 illustrates a methodology for registering a 3-D computed tomography (CT) image with a dual-energy image in accordance with an aspect of the invention.

FIG. 3 illustrates a methodology 60 for registering a 3-D CT image with a DEDR image in accordance with an aspect of the invention. The correlation of the DEDR images with a three-dimensional CT image provides improved sensitivity and specificity of dual-energy digital radiography. This correlation technique can be employed to train residents to find cardiac calcification in a patient. At 62, a CT image volume is captured of at least a portion of a body of a patient. The CT scans can be multi-detector computed tomography (MDCT). The CT examinations can employ a variety of clinical indications using imaging protocols that varied considerably in slice thickness, radiographic technique, and presence or absence of intravenous (IV) contrast material.

At 63, 3D translations and rotations are performed to the CT volume. In one aspect of the invention, 11 parameters are optimized in the 3D translations and rotations, i.e. three translations and three angles for the CT volume and two translations, one rotation, and two scaling parameters for the DRR image. The Downhill Simplex method can be employed for the optimization. To translate the CT volume, the following matrix can be employed:

$$\begin{bmatrix} x' \\ y' \\ z' \\ 1 \end{bmatrix} = \begin{bmatrix} 1 & 0 & 0 & t_x \\ 0 & 1 & 0 & t_y \\ 0 & 0 & 1 & t_z \\ 0 & 0 & 0 & 1 \end{bmatrix} \cdot \begin{bmatrix} x \\ y \\ z \\ 1 \end{bmatrix} \quad \text{(EQ. 4)}$$

where (x,y,z) is the coordinate of a voxel in the CT volume and (x',y',z') is the new position after the transformation and $t_x$, $t_y$, and $t_z$ are translations along X, Y and Z directions. Three rotation operations of the CT volume can be expressed in the following matrices:

$$\begin{bmatrix} x' \\ y' \\ z' \\ 1 \end{bmatrix} = \begin{bmatrix} 1 & 0 & 0 & 0 \\ 0 & \cos\theta_x & -\sin\theta_x & 0 \\ 0 & \sin\theta_x & \cos\theta_x & 0 \\ 0 & 0 & 0 & 1 \end{bmatrix} \cdot \begin{bmatrix} x \\ y \\ z \\ 1 \end{bmatrix} \quad \text{(EQ. 5)}$$

$$\begin{bmatrix} x' \\ y' \\ z' \\ 1 \end{bmatrix} = \begin{bmatrix} \cos\theta_y & 0 & \sin\theta_y & 0 \\ 0 & 1 & 0 & 0 \\ -\sin\theta_y & 0 & \cos\theta_y & 0 \\ 0 & 0 & 0 & 1 \end{bmatrix} \cdot \begin{bmatrix} x \\ y \\ z \\ 1 \end{bmatrix} \quad \text{(EQ. 6)}$$

$$\begin{bmatrix} x' \\ y' \\ z' \\ 1 \end{bmatrix} = \begin{bmatrix} \cos\theta_z & -\sin\theta_z & 0 & 0 \\ \sin\theta_z & \cos\theta_z & 0 & 0 \\ 0 & 0 & 1 & 0 \\ 0 & 0 & 0 & 1 \end{bmatrix} \cdot \begin{bmatrix} x \\ y \\ z \\ 1 \end{bmatrix} \quad \text{(EQ. 7)}$$

$\theta_x$, $\theta_y$, and $\theta_z$ are the rotation angles about the X-, Y- and Z-axis, respectively.

At 64, the CT image volume is projected into an image plane. A digitally reconstructed radiography (DRR) image can be provided using projection methods, such as a Gaussian weighted projection method or an averaged-based projection method. In one aspect of the invention, a shear-warp factorization technique is employed to generate a DRR image at 64. In this technique, a viewing transformation is applied to simplify the projection processing. The algorithm uses a principal viewing axis to choose a set of CT voxel slices to be resampled and composited. It also determines the order of the slices along the front-to-back direction of the image volume.

In general, a perspective viewing transformation matrix $M_{view}$ includes a permutation P, a shift of the origin $T_{shift}$, a 3D perspective shear scale $M_{shear}$, and a 2D warp $M_{warp}$; and hence $M_{view} = M_{warp} \cdot M_{shear} \cdot T_{shift} \cdot P$. $M_{view}$ is a 4×4 affine viewing transformation matrix that transforms points from the object space to the image space. $M_{view}$ will be simplified as: $M_{view} = M_{warp} \cdot M_{shear}$ where $M_{shear}$ is the shear transformation, a product of a pure shear transformation $M_{sh}$ and a perspective scaling transformation $M_s$, i.e. $M_{shear} = M_s \cdot M_{sh}$. The pure shear transformation $M_{sh}$ is represented as:

$$M_{sh} = \begin{bmatrix} 1 & 0 & -\frac{e_x}{e_z} & 0 \\ 0 & 1 & -\frac{e_y}{e_z} & 0 \\ 0 & 0 & 1 & 0 \\ 0 & 0 & 0 & 1 \end{bmatrix} = \begin{bmatrix} 1 & 0 & 0 & 0 \\ 0 & 1 & 0 & 0 \\ 0 & 0 & 1 & 0 \\ 0 & 0 & 0 & 1 \end{bmatrix} \quad \text{(EQ. 8)}$$

The matrix is simplified because $e_x = 0$, $e_y = 0$ and $e_z = -\rho$ where $(e_x, e_y, e_z)$ is the coordinate of the tube focus in the object space. The perspective scaling transformation $M_s$ can be described as:

$$M_S = \begin{bmatrix} 1 & 0 & 0 & 0 \\ 0 & 1 & 0 & 0 \\ 0 & 0 & 1 & 0 \\ 0 & 0 & -\frac{1}{e_z} & 1 \end{bmatrix} = \begin{bmatrix} 1 & 0 & 0 & 0 \\ 0 & 1 & 0 & 0 \\ 0 & 0 & 1 & 0 \\ 0 & 0 & \frac{1}{\rho} & 1 \end{bmatrix} \quad \text{(EQ. 9)}$$

where $\rho$ is the distance between the tube focus and the image plane. Thus, the shear transformation matrix $M_{shear}$ can be described as:

$$M_{shear} = M_S \cdot M_{sh} = \begin{bmatrix} 1 & 0 & -\frac{e_x}{e_z} & 0 \\ 0 & 1 & -\frac{e_y}{e_z} & 0 \\ 0 & 0 & 1 & 0 \\ 0 & 0 & -\frac{1}{e_z} & 1 \end{bmatrix} = \begin{bmatrix} 1 & 0 & 0 & 0 \\ 0 & 1 & 0 & 0 \\ 0 & 0 & 1 & 0 \\ 0 & 0 & \frac{1}{\rho} & 1 \end{bmatrix} \quad \text{(Eq. 10)}$$

The warp transformation is the product of the view transformation matrix and the inverse of the shear transformation matrix.

$$M_{warp} = M_{view} \cdot M_{shear}^{-1} \quad \text{(EQ. 11)}$$

$$= M_{view} \cdot \begin{bmatrix} 1 & 0 & \frac{e_x}{e_z} & 0 \\ 0 & 1 & \frac{e_y}{e_z} & 0 \\ 0 & 0 & 1 & 0 \\ 0 & 0 & \frac{1}{e_z} & 1 \end{bmatrix}$$

$$= M_{view} \cdot \begin{bmatrix} 1 & 0 & 0 & 0 \\ 0 & 1 & 0 & 0 \\ 0 & 0 & 1 & 0 \\ 0 & 0 & -\frac{1}{\rho} & 1 \end{bmatrix}$$

The projection parameters utilized can be the same as for the real dual energy DR image acquisitions. The parameters include the distance between the X-ray tube's focus and the detector plane. After a coordinate system is setup for the projection, the location of the X-ray tube and the principal view axis can be determined. These parameters are used to compute the perspective transformation matrix.

Based on the shear-warp factorization technique, a variety of projection methods can be employed, including Gaussian weighted projection, threshold-based projection, average-based projection, and maximum intensity projection, for this particular application. Gaussian weighted projection uses a Gaussian function as the weighting function during the projection processing. The CT values within a calcification region can be described as a series of variables with an approximate Gaussian distribution. The image intensities within this region are described as I~N ($\mu$, $\sigma^2$) where $\mu$ is the mean intensity and $\sigma$ is the standard deviation. In order to find the most optimal parameters, a search for $\mu$ from 10 to 990 Hounsfield Units (HU) and $\sigma$ from 20 to 280 HU can be performed. For each pair of $\mu$ and $\sigma$ values, projection images of the whole chest along the posterior-anterior (PA) direction can be generated. A visually evaluation of the quality of the projection images can be performed. The images can be graded as excellent, good, fair and poor. Based on the grades, a determination can be made on which pair of $\mu$ and $\sigma$ better show calcification. The threshold-based projection method uses a predetermined CT value as the threshold during projection processing. The average-based projection (AVG) generates an average intensity along the projection line. The maximum intensity projection (MIP) method only displays the maximum intensity along the projection line. The methodology then proceeds to 66.

At 66, the 2D DRR projected image is transformed by rotating and translating the image. In one aspect of the invention, a 2D translation of the DRR image can be expressed in the matrix below:

$$\begin{bmatrix} x' \\ y' \\ 1 \end{bmatrix} = \begin{bmatrix} 1 & 0 & t_x \\ 0 & 1 & t_y \\ 0 & 0 & 1 \end{bmatrix} \cdot \begin{bmatrix} x \\ y \\ 1 \end{bmatrix} \quad \text{(EQ. 12)}$$

where $t_x$, and $t_y$ are the translations along X and Y directions, respectively.
The 2D rotation of the DRR image is described below:

$$\begin{bmatrix} x' \\ y' \\ 1 \end{bmatrix} = \begin{bmatrix} \cos\theta & -\sin\theta & 0 \\ \sin\theta & \cos\theta & 0 \\ 0 & 0 & 1 \end{bmatrix} \cdot \begin{bmatrix} x \\ y \\ 1 \end{bmatrix} \quad \text{(EQ. 13)}$$

where $\theta$ is the rotation parameter of the 2D DRR image.
The 2D scaling operation can be described in the following matrix:

$$\begin{bmatrix} x' \\ y' \\ 1 \end{bmatrix} = \begin{bmatrix} s_x & 0 & 0 \\ 0 & s_y & 0 \\ 0 & 0 & 1 \end{bmatrix} \cdot \begin{bmatrix} x \\ y \\ 1 \end{bmatrix} \quad \text{(Eq. 14)}$$

As shown above, the 3D-to-2D registration has 11 degrees of freedom. These parameters describe the spatial relationship and geometric transformation between the 3D CT volume and the 2D DEDR image. These parameters may be reduced if the image acquisition parameters are known. For example, the two scales can be reduced to one if the scaling is the same in the X and Y directions. This will reduce the computation and speed up the registration.

At 68, the DRR image and a DEDR image are measured for similarities. Normalized mutual information (NMI) can be employed as the similarity measure because it is a robust similarity for many applications and because it does not assume a linear relationship between the gray values of two images.

Assuming that the DEDR image is a reference image (R), and the DRR image is a floating image (F). The NMI value can be calculated using the following equation:
where $$NMI(R, F) = \frac{2MI(R, F)}{H(R) + H(F)} \quad \text{(EQ. 15)}$$

$$H(R) = -\sum_r p_R(r)\log p_R(r) \quad \text{(EQ. 16)}$$

$$H(F) = -\sum_f p_F(f)\log p_F(f) \quad \text{(EQ. 17)}$$

$$MI(R, F) = \sum_{r,f} p_{RF}(r, f)\log \frac{p_{RF}(r, f)}{p_R(r) \cdot p_F(f)} \quad \text{(EQ. 18)}$$

The joint probability $p_{RF}(r,f)$ and the marginal probabilities $P_R(r)$ of the reference image and the $p_F(f)$ of the floating image can be estimated from the normalized joint intensity histograms. When two images are geometrically aligned, NMI is maximal.

At 70, an optimization routine is then run on the two-dimensional DRR image to register the two-dimensional DRR image with the DEDR image. Optimization of registration ends either when the maximum number of NMI calculations is reached (typically 500) or the fractional change in NMI is smaller than a tolerance (typically 0.0001). A downhill simplex method can be employed as a search strategy to align the dual-energy image with the reconstructed image. The projection at 64, the transformation at 66, the similarity measurement at 68 and the optimization at 70 are repeated until the results are satisfactory. Cardiac calcification can be more readily determined from the DRR image relative to the DEDR image.

Figure 4:
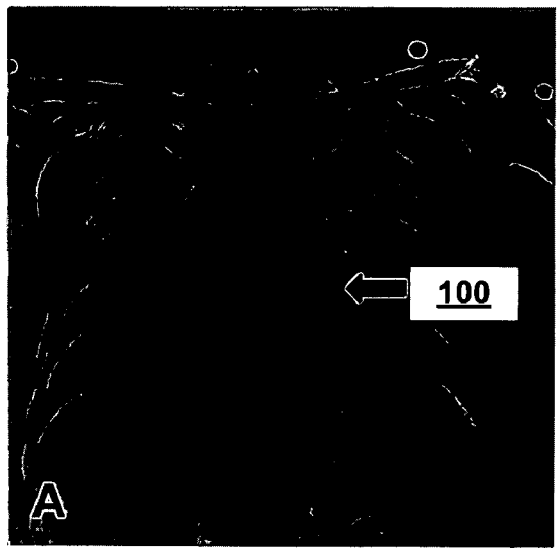
FIG. 4 illustrates a set of images associated with the methodology of FIG. 2 in accordance with an aspect of the invention.
Figure 4:
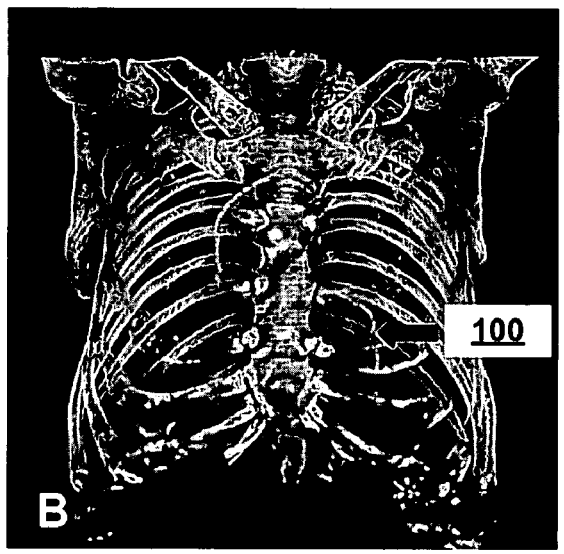
Figure 4:
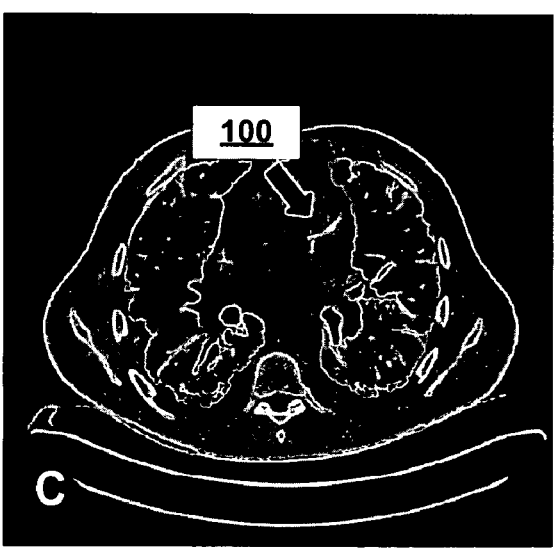
Figure 4:
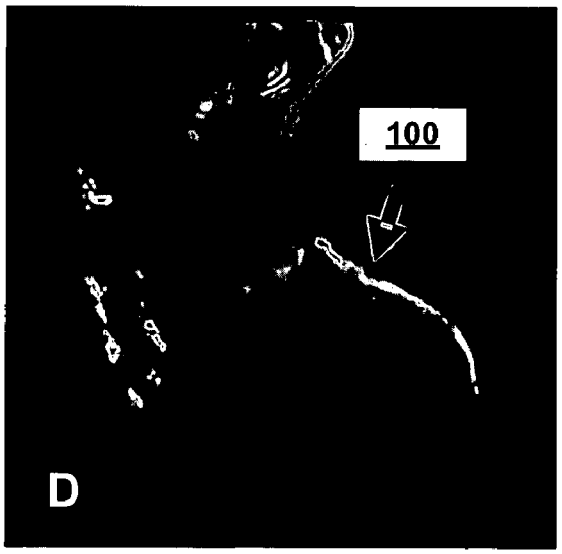

FIG. 4 illustrates a set of images associated with the methodology of FIG. 3 in accordance with an aspect of the invention. Image A is a DEDR image. An arrow 100 indicates a possible cardiac calcification. Experienced radiologists may be able to identify the cardiac calcification. However, in many cases, it can be difficult to exactly locate the cardiac calcification. Image C is a CT image. The calcification is clearly visible on the CT image (arrow). Thus, the CT image can be used as a gold standard to verify the location and evaluate the diagnostic result from dual-energy digital radiography. Using the CT image, a three-dimensional volume rendering of the heart can be generated (Image D). The coronary artery calcification is clearly visible (arrow). In Image B, the DRR image from the CT also illustrates the exact location of the coronary artery calcification.

Figure 5:
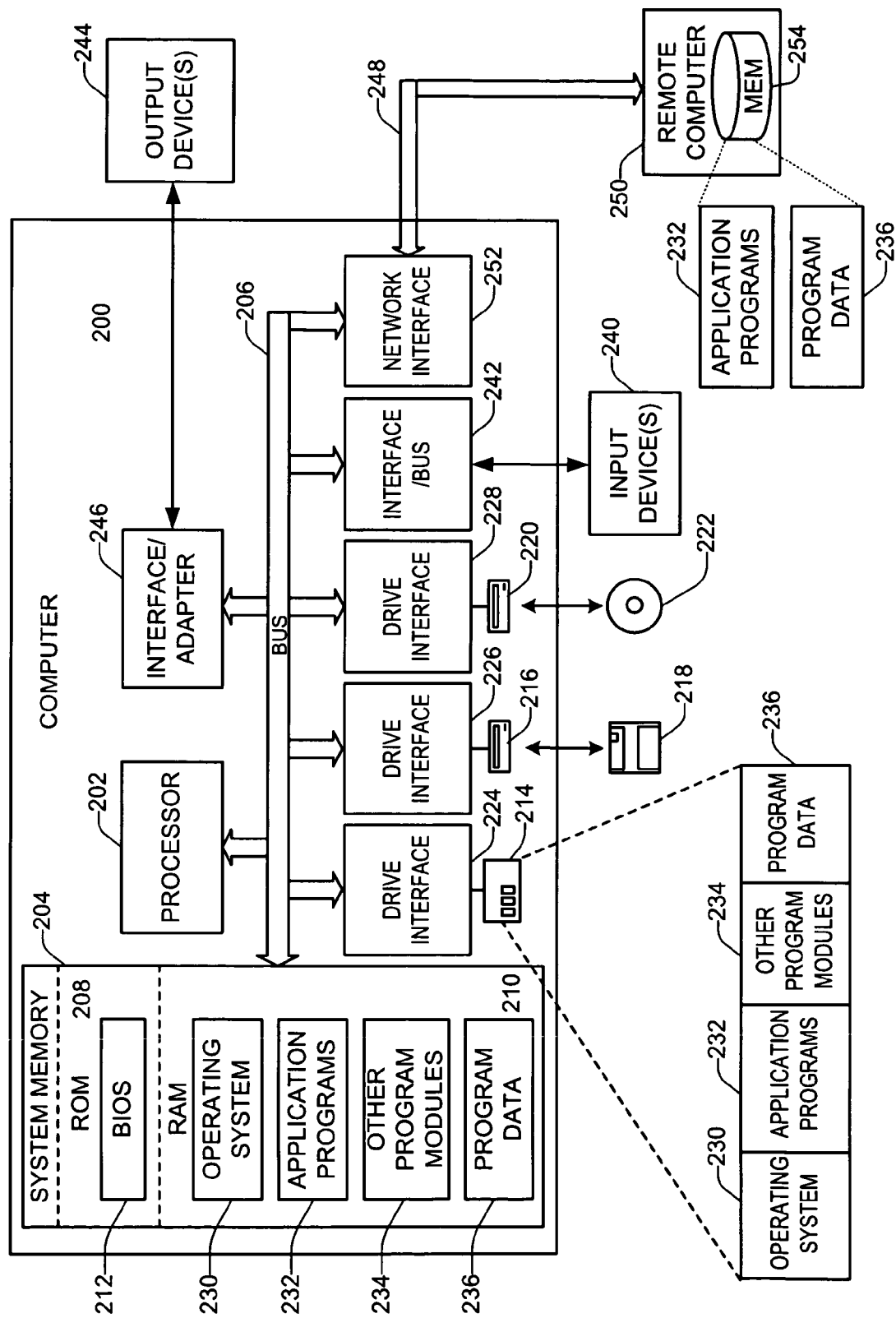
FIG. 5 illustrates a computer system that can be employed to implement systems and methods in accordance with one or more aspects of the invention.

FIG. 5 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems.

Additionally, the computer system 200 can be implemented as part of the computer-aided engineering (CAE) tool running computer executable instructions to perform a method as described herein.

The computer system 200 includes a processor 202 and a system memory 204. A system bus 206 couples various system components, including the system memory 204 to the processor 202. Dual microprocessors and other multi-processor architectures can also be utilized as the processor 202. The system bus 206 can be implemented as any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) 212 can reside in the ROM 208, generally containing the basic routines that help to transfer information between elements within the computer system 200, such as a reset or power-up.

The computer system 200 can include a hard disk drive 214, a magnetic disk drive 216, e.g., to read from or write to a removable disk 218, and an optical disk drive 220, e.g., for reading a CD-ROM or DVD disk 222 or to read from or write to other optical media. The hard disk drive 214, magnetic disk drive 216, and optical disk drive 220 are connected to the system bus 206 by a hard disk drive interface 224, a magnetic disk drive interface 226, and an optical drive interface 228, respectively. The drives and their associated computer-readable media provide nonvolatile storage of data, data structures, and computer-executable instructions for the computer system 200. Although the description of computer-readable media above refers to a hard disk, a removable magnetic disk and a CD, other types of media which are readable by a computer, may also be used. For example, computer executable instructions for implementing systems and methods described herein may also be stored in magnetic cassettes, flash memory cards, digital video disks and the like.

A number of program modules may also be stored in one or more of the drives as well as in the RAM 210, including an operating system 230, one or more application programs 232, other program modules 234, and program data 236. The one or more application programs can include the system and methods of generating DEDR X-ray images and registering 3D CT images with a DEDR X-ray image as previously described in FIGS. 1-4.

A user may enter commands and information into the computer system 200 through user input device 240, such as a keyboard, a pointing device (e.g., a mouse). Other input devices may include a microphone, a joystick, a game pad, a scanner, a touch screen, or the like. These and other input devices are often connected to the processor 202 through a corresponding interface or bus 242 that is coupled to the system bus 206. Such input devices can alternatively be connected to the system bus 206 by other interfaces, such as a parallel port, a serial port or a universal serial bus (USB). One or more output device(s) 244, such as a visual display device or printer, can also be connected to the system bus 206 via an interface or adapter 246. The computer system 200 may operate in a networked environment using logical connections 248 to one or more remote computers 250. The remote computer 250 may be a workstation, a computer system, a router, a peer device or other common network node, and typically includes many or all of the elements described relative to the computer system 200. The logical connections 248 can include a local area network (LAN) and a wide area network (WAN).

When used in a LAN networking environment, the computer system 200 can be connected to a local network through a network interface 252. When used in a WAN networking environment, the computer system 200 can include a modem (not shown), or can be connected to a communications server via a LAN. In a networked environment, application programs 232 and program data 236 depicted relative to the computer system 200, or portions thereof, may be stored in memory 254 of the remote computer 250.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Having described the invention the following is claimed:

1. A method for generating images for identifying diseases, the method comprising:
   receiving a first digital radiography (DR) X-ray image of at least a portion of a body of a patient;
   receiving a second DR X-ray image of the at least a portion of a body of a patient, the first X-ray image being captured at a different energy level than the second DR X-ray image;
   determining common control point locations for both the first and second DR X-ray images;
   generating an optimized DR X-ray image by moving portions of a selected one of the first and second DR X-ray images with its associated control points to locations that correspond to similar portions of the other of the first and second DR X-ray images;
   applying deformable transformation to one of the first and second DR X-ray images; and
   performing a log subtraction on the first and second DR X-ray image to generate a dual-energy digital radiography (DEDR) image.

2. The method of claim 1, wherein the performing a log subtraction on the first and second DR X-ray image to generate a DEDR image comprises performing a bone log subtraction on the first and second DR X-ray image to generate a bone image.

3. The method of claim 2, further comprising performing a soft tissue log subtraction on the first and second DR X-ray image to generate a soft tissue image.

4. The method of claim 1, wherein the determining common control point locations for both the first and second DR X-ray images comprises dividing the first and second DR X-ray image into a plurality of grids, such that each grid of the first DR X-ray image has an associated grid in the second DR X-ray image, and determining a common center point for each of the plurality of grids for both the first and second DR X-ray image.

5. The method of claim 1, wherein the determining common control point locations for both the first and second DR X-ray images comprises determining common edge features of the first and second DR X-ray images.

6. The method of claim 1, wherein the applying deformable transformation to one of the first and second DR X-ray images comprises performing one of a TPS algorithm and a B-spline algorithm on the one of the first and second DR X-ray images.

7. The method of claim 1, further comprising receiving a three-dimensional computer tomography (CT) image and registering the three-dimensional CT image with the DEDR image.

8. The method of claim 7, further comprising:
   performing a 3-dimensional (3D) translation and rotation on the CT image;

projecting the CT image onto an image plane to generate a 2-dimensional (2D) digitally reconstructed radiography (DRR) image;

performing a 2D transformation on the 2D DRR image;

measuring similarities of the 2D DRR with the DEDR image; and optimizing the registration of the 2D DRR with the DEDR image.

9. The method of claim 1, further comprising reviewing the dual-energy image to detect areas of cardiac calcification.

10. The method of claim 1, further comprising reviewing a digitally reconstructed radiography (DRR) image constructed from a three-dimensional computer tomography (CT) image to determine the validity of the detected areas of cardiac calcification in the DEDR image.

11. A computer readable computer having computer executable instructions for performing the method of claim 1.

12. A system for generating images for identifying diseases, the system comprising:

a control point optimization component configured to receive a first digital radiography (DR) X-ray image captured at a first energy level and a second DR X-ray image captured at a second energy level of at least a portion of a body of a patient and configured to optimize a DR X-ray image by moving portions of a selected one of the first and second DR X-ray images to locations that correspond to similar portions of the other of the first and second DR X-ray images;

a deformable transformation component that applies a deformable transformation to one of the first and second DR X-ray images; and a log subtraction component that performs a log subtraction on the first and second DR X-ray image to generate a dual-energy digital radiography (DEDR) image.

13. The system of claim 12, wherein the log subtraction component performs at least one of a bone log subtraction to generate a bone image and a soft tissue log subtraction to generate a soft tissue image.

14. The system of claim 12, wherein the control point optimization component is configured to locate common control point locations for both the first and second DR X-ray images by dividing the first and second DR X-ray image into a plurality of grids, such that each grid of the first DR X-ray image has an associated grid in the second DR X-ray image, and determining a common center point for each of the plurality of grids for both the first and second DR X-ray image.

15. The system of claim 12, wherein the control point optimization component is configured to locate common control point locations for both the first and second DR X-ray images by determining common edge features of the first and second DR X-ray image.

16. The system of claim 12, wherein the deformable transformation component is configured to perform one of a TPS algorithm and a B-spline algorithm on the one of the first and second DR X-ray images.

* * * * *

UNITED STATES PATENT AND TRADEMARK OFFICE
CERTIFICATE OF CORRECTION

| | |
|---|---|
| PATENT NO. | : 8,073,230 B2 |
| APPLICATION NO. | : 12/118232 |
| DATED | : December 6, 2011 |
| INVENTOR(S) | : Baowei Fei and Robert Gilkeson |

It is certified that error appears in the above-identified patent and that said Letters Patent is hereby corrected as shown below:

Title page, item [60] should read as follows:

Related U.S. Application Data

Provisional application No. 60/916,854, filed on May 9, 2007

Signed and Sealed this
Eighteenth Day of December, 2012

David J. Kappos
*Director of the United States Patent and Trademark Office*